United States Patent [19]
Jacobs et al.

[11] Patent Number: 5,939,085
[45] Date of Patent: Aug. 17, 1999

[54] SKIN SMOOTHING COMPOSITIONS CONTAINING HYDROXYACIDS AND METHODS FOR USING SAME

[75] Inventors: Michelle Matathia Jacobs, Syosset; Peter J. Lentini, Bayside, both of N.Y.

[73] Assignee: E-L Management Corp, New York, N.Y.

[21] Appl. No.: 08/972,649

[22] Filed: Nov. 18, 1997

Related U.S. Application Data

[63] Continuation of application No. 08/595,618, Feb. 2, 1996, abandoned.

[51] Int. Cl.[6] ....................................................... A61K 7/48
[52] U.S. Cl. ............................ 424/401; 424/43; 514/844; 514/846; 514/937; 514/944
[58] Field of Search ...................... 424/401, 43; 514/937, 514/844, 846, 944

[56] References Cited

U.S. PATENT DOCUMENTS

| | | | |
|---|---|---|---|
| 4,812,253 | 3/1989 | Small et al. | 252/32 |
| 4,848,576 | 7/1989 | Verdicchio et al. | 424/59 |
| 5,002,680 | 3/1991 | Schmidt et al. | 252/90 |

*Primary Examiner*—Jyothsna Venkat
*Attorney, Agent, or Firm*—Karen A. Lowney, Esq.

[57] ABSTRACT

Disclosed are skin smoothing compositions containing hydroxyacids or hydroxyacid derivatives, a polymeric film-forming agent, a physical exfoliant, and a pharmaceutically acceptable carrier. Also disclosed are methods for using the skin smoothing compositions to improve the smoothness of human skin.

12 Claims, No Drawings

SKIN SMOOTHING COMPOSITIONS CONTAINING HYDROXYACIDS AND METHODS FOR USING SAME This application is a continuation of application Ser. No. 08/595,618 filed Feb. 2, 1996 which application is now abandoned.

FIELD OF THE INVENTION

The present invention relates in genera to skin smoothing compositions, and in particular to skin smoothing compositions containing hydroxyacids. The invention additionally relates to a method for using such compositions to increase the smoothness of human skin.

BACKGROUND OF THE INVENTION

One of the goals of cosmetic science has long been the development of products capable of increasing the actual and/or perceived smoothness of human skin. Such skin smoothing compositions have traditionally contained physical exfoliants such as luffa and apricot kernel paste which, when rubbed against the skin, facilitate the rapid dislodging of debris and dead cells from the skin surface. The dislodged material is then removed from the skin surface along with the spent product, for example by the action of wiping, rinsing or washing, leaving behind a smoother, cleaner skin surface.

A more recent phenomenon in cosmetic science has been the development of products containing hydroxyacids; see C. D. Wheeler, *Soap/Cosmetics/Chemical Specialties*, 71 (2), 24 (1995). Hydroxyacids have been shown to be useful in the topical treatment of a variety of dermatological disorders, such as ichthyosiform dermatoses, dry skin and acne. While the exact mechanism of action of hydroxyacids on the skin is not known, it is generally believed that these materials are able to accelerate skin cell turnover by chemically exfoliating the dead cells on the skin surface over a period of days or weeks.

The ready availability of hydroxyacids from natural sources, such as citrus fruits, sugar cane and sour milk, as well as their favorable safety and efficacy profiles, have contributed to the widespread acceptance of hydroxyacid-containing products by consumers. Consumers have also come to expect and demand that such products be chemically and physically stable for long periods of time, easily applied to the skin, non-irritating and aesthetically pleasing upon application, in addition to being safe and efficacious.

Hydroxyacids commonly employed in cosmetic products may be broadly classified as being either alpha-hydroxyacids, wherein the hydroxyl group is situated on a carbon adjacent to the carbonyl carbon, or beta-hydroxyacids, wherein the hydroxyl group is situated on a carbon which is two carbons away from the carbonyl carbon. The most commonly used alpha-hydroxyacids in cosmetic products are those having a relatively small carbon backbone and low molecular weight, especially lactic acid (2-hydroxypropanoic acid), glycolic acid (hydroxyacetic acid), citric acid (2-hydroxy-1,2,3-propanetricarboxylic acid) and tartaric acid (2,3-dihydroxybutanedioic acid). The most commonly used beta-hydroxyacid in cosmetic products is salicylic acid (2-hydroxybenzoic acid).

It would be highly advantageous to exploit the chemical exfoliant properties of hydroxyacids in skin smoothing compositions containing physical exfoliants. Unfortunately hydroxyacids, and in particular the low molecular weight alpha-hydroxyacids referred to hereinabove, are significantly soluble in water and aqueous mixtures by virtue of their polar hydroxyl and carboxyl groups. Consequently, the long-term benefits which may be achieved by the use of hydroxyacids in skin smoothing compositions are limited by the facility with which the hydroxyacids are removed from the skin surface in the course of wiping, rinsing or washing. This is a particularly crucial drawback when low molecular weight hydroxyacids are formulated into skin smoothing compositions formulated with high levels of skin-cleansing surfactants, which may further increase the water solubility of the hydroxyacids.

SUMMARY OFT INVENTION

It is therefore an object of the present invention to provide novel skin smoothing compositions containing hydroxyacids. It is a further object of this invention to provide a method for using such compositions to increase the smoothness of human skin.

These and related objects of the present invention are achieved by providing skin smoothing compositions comprising:

(a) from about 0.5 to about 15.0 weight percent of a hydroxyacid;

(b) from about 0.1 to about 5.0 weight percent of a polymeric film forming agent;

(c) from about 5.0 to about 30.0 weight percent of a physical exfoliant; and (d) from about 50.0 to about 94.4 weight percent of a pharmaceutically acceptable carrier.

The present invention additionally relates to a method for using skin smoothing compositions containing hydroxyacids to improve the smoothness of human skin.

It is a surprising and unexpected discovery of the present invention that the incorporation of polymeric film-forming agents into skin smoothing compositions containing hydroxyacids provides compositions possessing an improved ability to increase the smoothness of human skin. The precise mechanism of this improvement is not known; however, without being limited by theory it is believed that the film forming agents increase the resistance of the hydroxyacids in the compositions towards removal from the skin by wiping, rinsing or washing. In addition, the film-forming agents may also function in the compositions of the present invention as auxiliary skin smoothing agents by coating the skin with a smooth, continuous polymeric film which is resistant to removal by wiping, rinsing or washing.

The skin smoothing compositions of the present invention are chemically and physically stable, non-irritating and aesthetically pleasing upon application. They may be readily formulated by the art skilled into any of a variety of cosmetic product forms, including but not limited to solutions, colloidal dispersions, emulsions, suspensions, creams, lotions, gels, aerosol foams, mousses and the like.

DETAILED DESCRIPTION OF THE INVENTION

In accordance with the present invention there are provided skin smoothing compositions comprising:

(a) from about 0.5 to about 15.0 weight percent of a hydroxyacid;

(b) from about 0.1 to about 5.0 weight percent of a polymeric film-forming agent;

(c) from about 5.0 to about 30.0 weight percent of a physical exfoliant; and (e) from about 50.0 to about 94.4 weight percent of a pharmaceutically acceptable carrier.

The compositions of this invention comprise from about 0.5 to about 15.0 weight percent, preferably from about 1.0 to about 3.0 weight percent, most preferably about 2.5 weight percent of a hydroxyacid. The term "hydroxyacid" for purposes of the present invention encompasses alpha-hydroxyacids and beta-hydroxyacids in their free acid form, as well as covalent derivatives thereof. Suitable hydroxyacids include, but are not limited to, alpha-hydroxyacids such as lactic acid, glycolic acid, citric acid, alpha-hydroxyoctanoic acid, alpha-hydroxydecanoic acid, alpha-hydroxylauric acid, tartaric acid, glucoronic acid, galactouronic acid, alpha-hydroxybutyric acid, alpha-hydroxyisobutyric acid, malic acid, mandelic acid, mucic acid, pyruvic acid and tartronic acid, especially lactic acid, glycolic acid, citric acid, mandelic acid, alpha-hydroxyoctanoic acid, alpha-hydroxydecanoic acid, and alpha-hydroxylauric acid, most especially lactic acid and citric acid; beta-hydroxyacids such as salicylic acid; and mixtures thereof especially mixtures of lactic acid, alpha-hydroxyoctanoic acid, alpha-hydroxydecanoic acid and alpha-hydroxylauric acid. Suitable covalent derivatives of hydroxyacids include esters, amides and lactones thereof, and mixtures thereof.

The compositions of the present invention additionally comprise from about 0.1 to about 5.0 weight percent, preferably from about 0.2 to about 1.0 weight percent, most preferably about 0.3 weight percent of a polymeric film forming agent. In a preferred embodiment of the invention the polymeric film forming agent is a polymeric quaternium ammonium salt. Suitable polymeric film forming agents for purposes of the present invention include, but are not limited to: polyquaternium7, a polymeric quaternary ammonium salt consisting of acrylamide and dimethyl diallyl chloride monomers, available commercially under the trade name Merquat (Calgon Corporation, Pittsburgh, Pa.); and polyquaternium-10, a polymeric quaternary salt of hydroxyethylcellulose reacted with a trimethyl ammnonium substituted epoxide, available commercially under the tradename UCARE Polymer JR (Amerchol Corporation, Edison, N.J.).

The compositions of the present invention additionally comprise from about 5.0 to about 30.0 weight percent of a physical exfoliant. The term "physical exfoliant" as used herein refers to any pharmaceutically acceptable particulate substance which may be rubbed against skin to facilitate the removal of dirt and/or dead cells from the skin surface. Suitable physical exfoliants include, but are not limited to: natural waxes having a melting point of greater than about 70° C., especially carnauba, ozokerite, montan wax and beeswax; synthetic waxes having a melting point of greater than about 70° C., especially polyethylene and synthetic carnauba; fruit and vegetable derivatives such as almond meal, apricot shell powder, corn flour, corn meal, pecan shell powder, peach pit powder, walnut shell powder, and luffa; and non-wax abrasives such as diatomaceous earth, hydrated silica and hydroxyapatite, especially polyethylene, carnauba, synthetic carnauba, montan wax, and mixtures thereof. A synthetic carnauba preparation is available commercially under the tradename Wax 124 Synthetic Carnauba from Whittaker, Clark & Daniels, Inc. (South Plainfield, N.J.).

The compositions of the present invention additionally comprise from about 50.0 to about 94.4 weight percent of a pharmaceutically acceptable carrier. The term "pharmaceutically acceptable carrier" as used herein refers to a vehicle for delivering the hydroxyacid, the polymeric film forming agent, and the physical exfoliant to the skin, which is comprised of materials that are not known to be harmful to humans. The pharmaceutically acceptable carrier can be in the form of including but not limited to, an aerosol foam, mousse, cream, lotion, gel mask or emulsion.

In a preferred embodiment of this invention the pharmaceutically acceptable carrier is an oil-in-water emulsion. Such emulsions comprise one or more oil components and an oil-in-water emulsifier component dispersed within an aqueous component, wherein the oil-in-water emulsifier component comprises at least one oil-in-water emulsifier, i.e., an emulsifier having a hydrophilic-lipophilic balance ("HLB") of at least 6. The oil-in-water emulsifier component may also comprise a mixture of one or more oil-in-water emulsifiers and one or more water-in-oil emulsifiers (i.e., emulsifiers having an HLB of from about 2 to about 6), in which case the type and amount of each emulsifier present in the mixture is selected such that the effective HLB of the resultant oil-in-water emulsifier component is at least about 6. Techniques for combining and ascertaining the effective HLB of a mixture of emulsifiers are known; see L. M. Prince, in M. G. DeNavarre, "The Chemistry and Manufacture of Cosmetics," Volume III, Second Ed. (Continental Press, Orlando, 1975), pp. 25–37.

Suitable oil-in-water emulsifiers include, but are not limited to, sorbitol derivatives such as sorbitan monolaurate and polysorbate 20; ethoxylated alcohols such as laureth-23; ethoxylated fatty acids such as PEG-100 stearate; amidoamine derivatives such as stearamidoethyl diethylamine; sulfate esters such as sodium lauryl sulfate; phosphate esters such as DEA cetyl phosphate; fatty acid amine salts such as TEA stearate; and mixtures thereof.

Suitable water-in-oil emulsifiers include, but are not limited to, glyceryl esters such as glyceryl stearate, glyceryl caprylate, glyceryl oleate and glyceryl dioleate; glycol esters such as propylene glycol stearate; beeswax derivatives such as PEG-8 beeswax; lactylate derivatives such as sodium isostearoyl-2 lactylate; lecithin, and mixtures thereof.

In a particularly preferred embodiment the oil-in-water emulsifier component comprises a mixture of the oil-in-water emulsifier stearamidoethyl diethylamine and the water-in-oil emulsifier glyceryl stearate. Such a mixture is available commercially under the tradename Lexemul AR from Inolex Chemical Co. (Philadelphia, Pa.).

In an especially preferred embodiment the emulsifier component additionally comprises one or more emulsifiers having an HLB of from about 15 to about 70. Such high-HLB emulsifiers, referred to hereinafter as "surfactants," function in the compositions of the present invention both as oil-in-water emulsion stabilizers and as skin smoothing agents. Suitable surfactants include, but are not limited to disodium cocoamphodiacetate, available commercially as a 39% aqueous solution under the tradename Miranol C2M-NP (RTD Chemical Corp., Hackettstown, N.J.), disodium oleamido MIPA-sulfosuccinate, available commercially as a 38% aqueous solution under the tradename Soleterge 8 (Strahl & Pitsch, West Babylon, N.Y.), and mixtures thereof.

Suitable oil components include, but are not limited to, natural oils, such as coconut oil; hydrocarbons, such as mineral oil and hydrogenated polyisobutene; fatty alcohols, such as octyldodecanol; esters, such as myristyl lactate; diesters, such as propylene glycol; triesters, such as glyceryl trioctanoate; sterol derivatives, such as lanolin; and mixtures thereof.

Suitable oil components may also be silicones, including, but not limited to, volatile silicones, such as cyclomethicone; non-volatile silicones, such as dimethicone and dimethiconol; and derivatives thereof.

The pharmaceutically acceptable carrier can additionally include one or more optional ingredients known to those skilled in the art, such as preservatives, fragrances, emollients, antiseptics, antiinflammatories, antibacterials, stabilizers, antioxidants, vitamins, pigments, dyes, humectants, and propellants, as well as other classes of materials whose presence in the compositions of the inventions may be cosmetically, medicinally or otherwise desirable. Such materials can be found in the CTFA International Cosmetics Ingredients Dictionary (The Cosmetic, Toiletry and Fragrance Association, Washington, D.C., 1991) and equivalent sources.

The present invention additionally relates to a method for using skin smoothing compositions containing hydroxyacids to increase the smoothness of human skin, which method comprises applying a composition of the invention to the skin, rubbing the composition against the skin for about one minute, a time generally sufficient to facilitate the dislodging of debris and dead cells from the skin surface, and removing the dislodged debris and dead cells from the skin together with the composition, preferably by the action of wiping, rinsing or washing.

The following non-limiting examples illustrate various embodiments of the present invention:

EXAMPLE 1

SKIN SMOOTHING COMPOSITION

| Ingredient | Weight Percent |
| --- | --- |
| Phase 1 | |
| Glyceryl Stearate/Stearamidoethyl Diethylamine | 11.50 |
| Glycol Stearate | 2.00 |
| Phenoxyethanol/Methyl Paraben/Ethyl Paraben/ Propyl Paraben/Butyl Paraben[1] | 1.00 |
| BHT | 0.10 |
| Myristyl Lactate | 1.50 |
| Phase 2 | |
| Magnesium Aluminum Silicate | 0.52 |
| Butylene Glycol | 1.00 |
| Purified Water | 15.98 |
| Phase 3 | |
| Polyquaternium-10 | 0.30 |
| Purified Water | 14.70 |
| Phase 4 | |
| Trisodium EDTA | 0.05 |
| Disodium Cocoamphodiacetate (39% Aq. Solution) | 20.00 |
| Phase 5 | |
| Disodium Oleamido MIPA-Sulfosuccinate (38% Aq. Solution) | 12.00 |
| Phase 6 | |
| Polyethylene | 11.00 |
| Phase 7 | |
| Titanium Dioxide | 0.26 |
| Butylene Glycol | 0.39 |
| Phase 8 | |
| Lactic Acid | 2.50 |
| Phase 9 | |
| Fragrance | 1.00 |
| Phase 10 | |
| Carnauba/Titanium Dioxide/D&C Red No. 30 Lake[2] | 4.00 |

[1]Phenonip (NIPA Hardwicke, Inc., Wilmington, DE)
[2]Florabeads Carnauba Wax/Peach (International Flora Technologies, Ltd., Gilbert, AZ)

Procedure

1. Phase 1 ingredients are combined in a primary vessel at 80° C. with mixing.
2. Phase 2 ingredients are combined in a secondary vessel at 78° C. with mixing.
3. The combined Phase 2 is added to the combined Phase 1 in the primary vessel at 75° C. with mixing, and the batch is slowly allowed to cool while mixing is continued.
4. Phases 3 through 10 are added sequentially to the primary vessel at the following temperatures: Phase 3 (70° C.), Phase 4 (60° C.), Phase 5 (55° C.), Phase 6 (45° C.), Phase 7 (45° C.), Phase 8 (45° C.), Phase 9 (45° C.), Phase 10 (43° C.)
5. Mixing is continued until the composition reaches a temperature of 30° C.

EXAMPLE 2

METHOD OF INCREASING SKIN SMOOTHNESS

Procedure

Nineteen women who possessed dry, scaly skin on the calf area were recruited for a single blinded study to evaluate the skin smoothing compositions of the present invention. Half of the women applied the skin smoothing composition of Example 1 to both calves once a day for a period of four weeks. The other half similarly applied to their calves a commercial skin smoothing composition, Estée Lauder Body Smoother Exfoliating Creme, containing 15% by weight of polyethylene as a physical exfoliant, as a control. The women were instructed to rub the products against the skin for about one minute, and then rinse the skin with lukewarm water. Baseline skin smoothness was assessed at the start of the study, and subsequent skin smoothness measurements were taken immediately after the first application of either the Example 1 or control skin smoothing compositions and at the end of four weeks, following the D-Squames/Image Analysis method of Schatz et al., *Dry Skin and Scaling Evaluated by D-Squames and Image Analysis, Handbook of Non-Invasive Methods and the Skin* (CRC Press, Boca Raton, London and Tokyo, 1995), pp 153–157. According to this method, dead cells on the skin surface are removed by tape stripping and quantified by an image analysis protocol; the amount of dead cells present on the skin surface is then interpreted as an inverse measure of the degree of skin smoothness.

Results

The ski smoothing composition of Example 1 improved skin smoothness by 49% and 41% immediately after the first application and at the end of four weeks, respectively. The control composition improved skin smoothness by 36% and 28% immediately after the first application and at the end of four weeks, respectively. A significant difference ($p<0.005$) favoring the composition of Example 1 over the control composition in improving skin smoothness was recorded at each time point.

While the present invention has been set forth in terms of specific embodiments thereof, it will be understood that numerous variations are now enabled to those skilled in the art. Accordingly, the invention is to be broadly construes and limited only by the scope of the appended claims.

What is claimed is:

1. A skin smoothing composition which comprises:
   (a) from about 0.5 to about 15.0 weight percent of a hydroxyacid selected from the group consisting of lactic acid, citric acid, salicylic acid, alpha-hydroxyoctanoic acid and alpha-hydroxylauric acid;
   (b) from about 0.1 to about 5.0 weight percent of a polymeric film forming agent selected from the group consisting of polyquaternium ammonium salts;

(c) from about 5.0 to about 30.0 weight percent of a physical exfoliant selected from the group consisting of polyethylene, carnauba, synthetic carnauba, montan wax, and walnut shell powder; and (d) from about 50.0 to about 94.4 weight percent of a pharmaceutically acceptable carrier.

2. The skin smoothing composition of claim 1 wherein the hydroxyacid is lactic acid.

3. The skin smoothing composition of claim 1 wherein the polymeric quaternium salt is polyquaternium-7.

4. The skin smoothing composition of claim 1 wherein the polymeric quaterinum salt is polyquaternium-10.

5. The skin smoothing composition of claim 1 which comprises from about 1.0 to 3.0 weight percent of the hydroxyacid.

6. The skin smoothing composition of claim 5 which comprises about 2.5 weight percent of the hydroxyacid.

7. The skin smoothing composition of claim 1 which comprises from about 0.2 to about 1.0 weight percent of the polymeric film forming agent.

8. The skin smoothing composition of claim 7 which comprises about 0.3 weight percent of the polymeric film forming agent.

9. The skin smoothing composition of claim 1 wherein the pharmaceutically acceptable carrier is an oil-in-water emulsion.

10. The skin smoothing composition of claim 9 wherein the oil-in-water emulsion comprises a surfactant.

11. The skin smoothing composition of claim 10 wherein the surfactant is selected from the group consisting of disodium cocoamphodiacetate and disodium oleamido MIPA-sulfosuccinate.

12. A method for increasing the smoothness of human skin which comprises the steps of:

(a) applying a skin smoothing composition comprising from about 0.5 to about 15.0 weight percent of a hydroxyacid selected from the group consisting of lactic acid, citric acid, salicylic acid, alpha-hydroxyoctanoic acid and alpha-hydroxylauric acid, from about 0.1 to about 5.0 weight percent of a polymeric film-forming agent selected from the group consisting of polyquaternium ammonium salts, from about 5.0 to about 30.0 weiqht percent of a physical exfoliant selected from the group consisting of polyethylene, carnauba, synthetic carnauba, montan wax, and walnut shell powder, and from about 50.0 to about 94.4 weiqht percent of a pharmaceutically acceptable carrier to human skin;

(b) rubbing the skin smoothing composition against the skin for a time sufficient to facilitate the dislodging of debris and dead cells from the skin surface; and (c) removing the dislodged debris and dead cells from the skin together with the skin smoothing composition from the skin by the action of wiping, rinsing or washing.

* * * * *